United States Patent [19]

Settler et al.

[11] Patent Number: 5,603,817
[45] Date of Patent: Feb. 18, 1997

[54] PH MEASURING SYSTEM

[76] Inventors: Bert Settler, 723 Queenston Street, Winnipeg Manitoba, Canada, R3N 0X8; Morris Settler, 590 Niagara Street, Winnipeg Manitoba, Canada, R3N 0V8

[21] Appl. No.: 489,512

[22] Filed: Jun. 12, 1995

[30] Foreign Application Priority Data

Jul. 10, 1994 [GB] United Kingdom .................. 9411701

[51] Int. Cl.⁶ .................................................. G01N 27/26
[52] U.S. Cl. .......................... 204/433; 204/435; 128/635; 128/642
[58] Field of Search .................................. 204/433, 435; 128/635, 642

[56] References Cited

U.S. PATENT DOCUMENTS

| | | | |
|---|---|---|---|
| 4,401,548 | 8/1983 | Brezinski | 204/435 |
| 4,406,766 | 9/1983 | MacDonald | 204/433 |
| 4,447,309 | 5/1984 | Morioka et al. | 204/435 |
| 4,477,330 | 10/1984 | Nielsen | 204/435 |
| 4,565,665 | 1/1986 | Fogt | 204/435 |
| 4,568,444 | 2/1986 | Nakamura et al. | 204/435 |
| 4,783,252 | 11/1988 | Benton | 204/435 |
| 4,834,101 | 5/1989 | Collison et al. | 204/433 |

*Primary Examiner*—Bruce F. Bell
*Attorney, Agent, or Firm*—Pascal & Associates

[57] ABSTRACT

A PH measuring device having a first and second lumen with adjacent first ends, wherein the first lumen has a sensor electrode secured to the first end and the second lumen has a fibrous absorbent plug closing the first end, with an absorbent thread attached to the plug, and extending through the second lumen. An electric conductor connected to the sensor electrode extends through the first lumen to an electrical meter.

18 Claims, 4 Drawing Sheets

5,603,817

PH MEASURING SYSTEM

The present invention relates to the measurement of pH and to an electrode for pH measurement.

Metal oxide electrodes are used in dentistry and medicine as sensors for measuring pH. The electrodes used are conventionally made from antimony. Generally they are used in a system including a reference half cell, a meter and connectors for coupling these components. Conventionally the reference electrode which must be attached to the organ or patient is defined by a second connecting wire and a contact located at a separate point on the patient. This is inconvenient and leads to inaccuracies in the measurement.

SUMMARY OF THE INVENTION

It is one object of the present invention to provide improvements in such electrodes and the systems in which they are used and particularly an electrode which allows the sensor contact and the reference contact to be located closely or immediately adjacent to improve efficiency and to provide improved accuracy.

According to one aspect of the present invention there is provided a pH measuring electrode comprising:

probe means for defining a first lumen and a second lumen with adjacent first ends;

a sensor electrode secured to the first end of the first lumen and exposed at the first end of the first lumen;

an electric conductor leading from the sensor electrode through the first lumen including means for electrical connection to an electrical meter for measuring an electrical value indicative of the pH to be measured;

a fibrous thread material extending along the second lumen;

means for electrically connecting the thread material to the electrical meter; and porous means closing the first end of the second lumen and electrically connected to the thread material.

When the thread is saturated with an electrolyte it acts as a salt bridge that can be connected to a reference half cell in the system. The close spacing of the bridge and the sensor electrode is desirable to ensure a quick response and to minimize drift.

Preferably, a chamber is secured to the tube. The lumen carrying the lead from the sensor electrode is isolated from the chamber, while the thread extends from the other lumen into the chamber. In use, the chamber and the thread carrying lumen are filled with an electrolytic gel. To provide adequate shelf life, this gel may be injected shortly before use through an access port provided in the chamber for that purpose.

According to another aspect of the present invention there is provided a pH measuring electrode comprising:

probe means for defining a first lumen and a second lumen with adjacent first ends;

a sensor electrode secured to the first end of the first lumen and exposed at the first end of the first lumen;

an electrical conductor leading from the sensor electrode through the first lumen including means for electrical connection to an electrical meter for measuring an electrical value indicative of the pH to be measured;

a chamber connected to the second lumen, the chamber being arranged to receive an electrolytic liquid;

electrical reference means in electrical connection with the electrolytic liquid means for electrically connecting the reference means to the electrical meter; and porous means closing the first end of the second lumen and electrically connected to the electrolytic liquid.

BRIEF DESCRIPTION OF THE DRAWINGS.

In the accompanying drawings, which illustrate an exemplary embodiment of the present invention.

DETAILED DESCRIPTION

Figure 1:
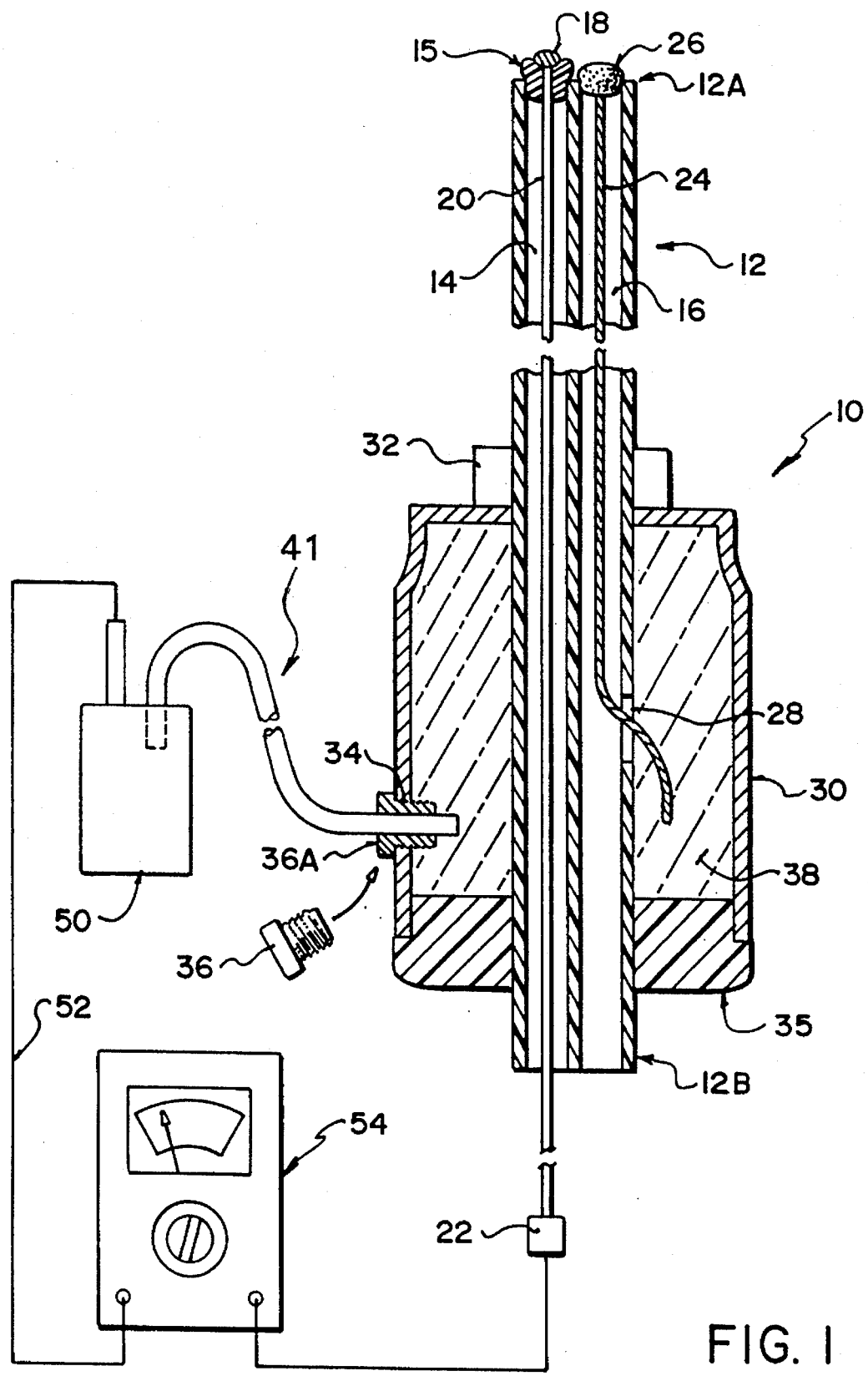
FIG. 1 is a schematic of a system according to the present invention.

Referring to the accompanying drawings, FIG. 1 illustrates a pH measuring system 10. This includes a double lumen teflon tube 12 including a sensor lumen 14 and a reference lumen 16. The tube, which is commercially available, is small enough in diameter to canulate through a sixteen gauge catheter and has an outer sensor end 12A and an opposed end 12B. The sensor lumen 14 and the reference lumen 16 can be seen in cross-section in FIG. 2. At the outer end 12A of the sensor lumen 14 is an antimony sensor electrode 18 that is sealed to the end of the lumen 14 by an epoxy resin 15. A conductive metal lead 20 is attached to and leads from the sensor electrode 18 through the sensor lumen 14 and is connected to an electrical connector 22 of conventional construction at the end 12B. The metal lead is formed of a suitable conductive metal such as copper with an insulating cover including an inner layer 20A bonded to the conductor and an outer teflon sheath 20B.

The other or reference lumen 16 has an absorbent thread 24 of cotton or similar fibrous material running along the lumen. At the tip end immediately adjacent the sensor 18 but electrically separated therefrom by the resin 15, the lumen 16 is closed with a fibrous absorbent plug 26 of cotton or similar material. The thread leaves the lumen 16 through a small hole 28 intermediate the ends of the tube.

Surrounding the tube 12 intermediate its ends and secured to it is a generally cylindrical reservoir chamber 30. The lumen 14 of the tube passes through the chamber to isolate the sensor electrode 18 and the lead 20 from the inside of the chamber. The chamber surrounds the hole 28 in the lumen 16 so that the interior of the chamber is in communication with the interior of the lumen 16 and so that the thread 24 emerging from the hole or window 28 terminates in the chamber 30.

Surrounding the tube 12, on the end of the reservoir chamber 30 is the female component of a standard leur lock fitting 32 to allow application of a covering cap over the outer end of the tube 12 which can be removed for use.

An access port 34 is formed in the side wall of the reservoir chamber 30 and is normally closed with a threaded plug 36. An end cap 35 is provided at an end of the chamber through which the tube 12 passes thus sealing the interior of the chamber in communication with the lumen 16. In this sealed and capped condition, the sensor element defined by the tube 12 and the reservoir 30 can be packaged and stored for use in a sterile condition.

In use of the system, as illustrated in FIG. 1, sensor element is removed from the packaging and the reservoir chamber 30 is filled from a suitable source, such as a separately packaged syringe, with a thixotropic electrolytic gel 38 saturated with potassium chloride (KCI). Some of the gel may enter the lumen 16 through the window 28 but it is not necessary to ensure a complete filling of the lumen. The thread 24 at its tail end in the chamber 30 is saturated with KCI solution and some of this will wick along the thread to the end plug 26.

Figure 3:
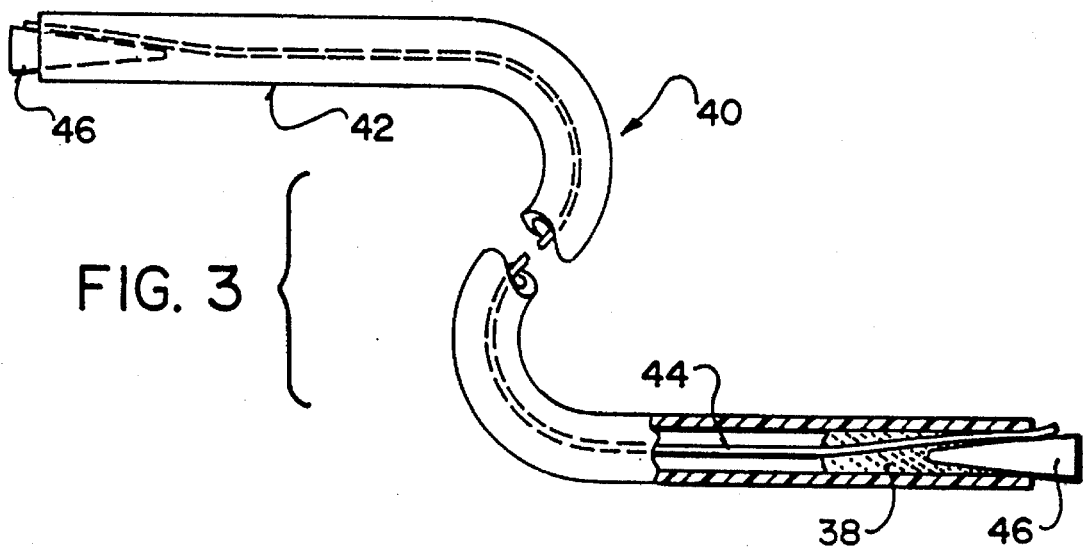
FIG. 3 is a side view, partially in cross section of the ion bridge.

With the plug 36 removed, one end of a bridge 41 is inserted through a guide plug 36A with a central bore into the chamber 30 to contact the gel 38. The configuration of this bridge is most particularly illustrated in FIG. 3. The bridge includes an outer polyethylene tube 42 with a cotton thread 44 extending along the tube from end to end. The thread is saturated with KCI and the tube is filled with the thixotropic KCI saturated gel 38 used in the reservoir 30 and the lumen 16. The ends of the tube 42 are closed with tapered wooden plugs 46. These constitute ion junctions at the ends of the completed bridge, each in the form of a non-metallic conductive plug at an end of the duct for electrically connecting gel in the chamber. Each plug is fibrous, porous and includes interstices impregnated with the liquid for allowing the liquid to provide conductivity through the plug, while the plug prevents bleeding or leeching of the liquid from the end of the tube. The cotton thread forms a continuous non-metallic thread extending longitudinally of the duct within the liquid.

As illustrated in FIG. 1, the end of the bridge opposite the reservoir 30 is inserted into the electrolyte in a standard calomel reference half cell 50. This is a known and widely used device acting as a reference voltage in comparison with the sensed voltage from the antimony electrode connected to the copper lead wire. The lead 52 from the electrode of the half cell is connected to a meter 54, as is the lead 20 from the sensor 18. The meter is a high input impedance volt meter calibrated to read directly in pH. In other embodiments, a standard volt meter can be used. The reference 50 is thus connected through the gel junction 38 to the cotton reference 24 that terminates at the sending end of the combination electrode.

Figure 4:
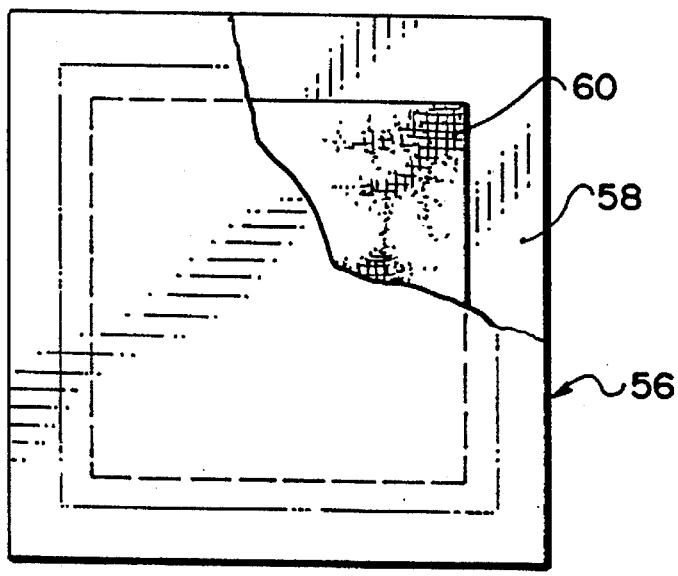
FIG. 4 is a front view, partially in section of a buffer pack.
Figure 5:
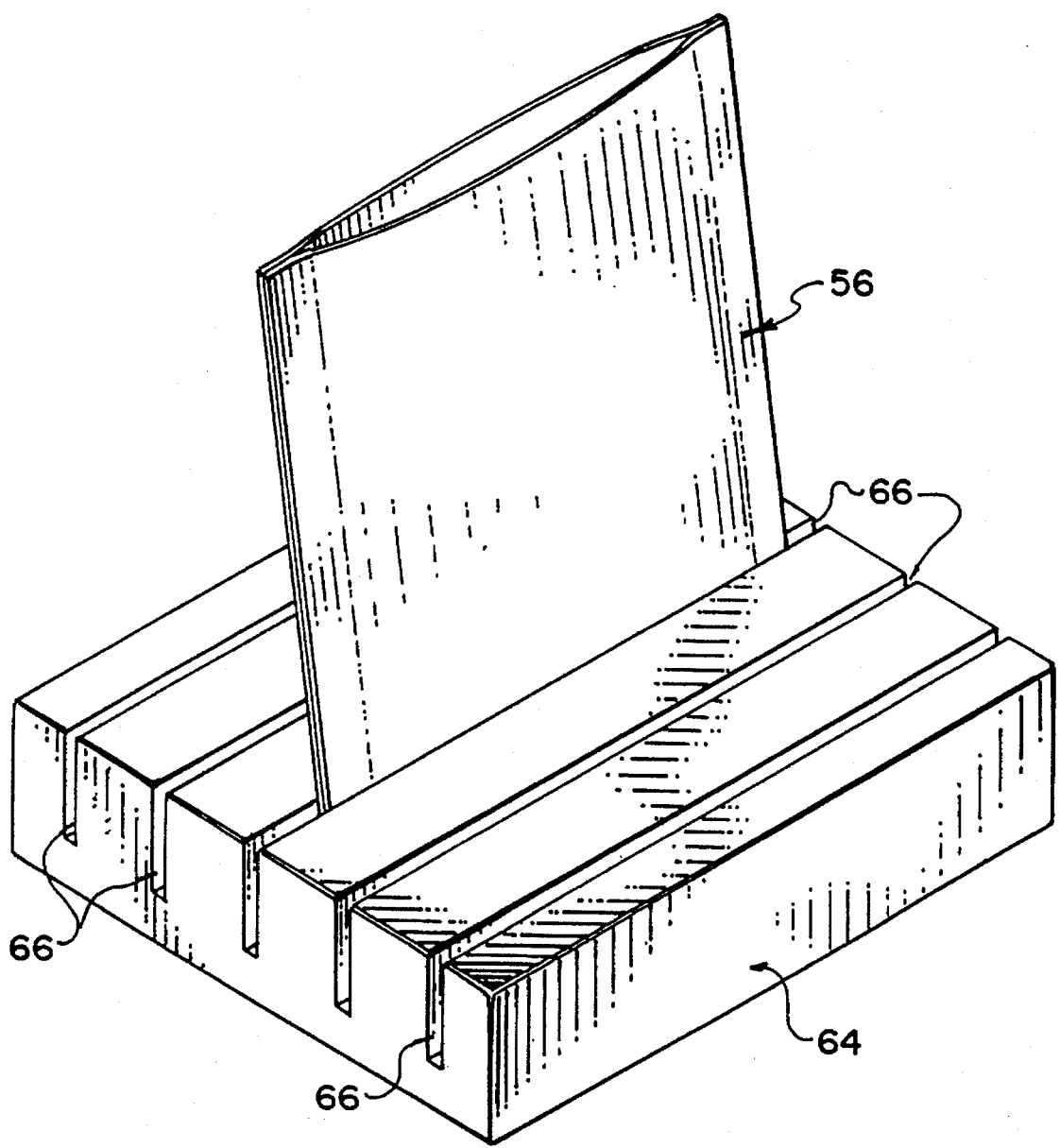
FIG. 5 is an isometric view of a support block supporting a buffer pack.

Because no two of the antimony electrodes are exactly alike, the system must be calibrated before use. To do this, three standard buffer solutions are used contained within respective buffer solution packs 56, one of which is illustrated in FIG. 4. One of these solutions has a pH of 6.84, another has a pH of 7.45. The third is a neutral solution with a pH of 7.0. A fourth package contains distilled water to rinse the electrode between tests. Calibration is done with the 6.84 and 7.45 pH solutions. The 7.0 pH solution is for testing after two point calibration has been done using the pH 6.84 and 7.45 solutions.

Each of the packs 56 is a flat foil envelope 58 containing the buffer solution and an internal pad 60 to support the envelope in a flat condition.

To support the buffer packs for use, a plastic support block 64 is provided with four parallel slots 66 that will receive the bottom edges of the respective packages 56 and support the envelopes in the upright position. This makes the envelopes extremely easy to use, minimizes spills of buffer and eliminates the use of glass and plastic containers which are prone to tipping and spilling their contents.

The ion bridge 40 described in the foregoing may also be sealed in a foil envelope similar to those containing the buffer solutions and the distilled water rinse. The ion bridge package contains a saturated solution of KC1. All of these packages can be sterilized using a linear accelerator to sterilization technique. They are perfectly sealed and can be stored for long periods.

Because the antimony electrode should be kept dry, the electrode assembly is not similarly packaged. However, because the KCI saturated gel will dry out and the KCI crystallize if not sealed and kept moist, the electrode is packaged dry, that is without the gel in the reservoir chamber 30 or the lumen 16. The gel is instead stored in a sealed syringe that may be fitted with a flexible injection tube that can be inserted through the access port 34 in the chamber 30 to inject the gel shortly before the electrode assembly is to be used.

As noted above, for physiological uses, the tube 12 of the combination electrode assembly can be installed through a 16 gauge catheter. For that purpose, the complete system includes a catheter placement unit and a catheter of standard configuration. The female leur lock fitting on the end of the chamber 30 is used in this environment, when the tube 12 is inserted through the catheter, to hold the electrode assembly in place. In use of the electrode, the sensor electrode 18 and the medium being measured form a half cell that communicates through the ion conductor bridge in lumen 16 with the reservoir chamber 30 and then through the ion bridge 40 with the electrolyte in the reference half cell 50. The cotton plug 26 in the end of lumen 16 prevents excess leaking or leaching of the KCI gel into the media being measured, but will conduct the ions necessary to complete the cell.

The physiological uses of the microsize antimony electrodes are threefold.

Firstly, in dentistry, for measuring the pH of:
(i) dental plaque, the bacterial deposits on the teeth and gums that are responsible for the development of cavities and periodontal disease;
(ii) saliva, which is an important indicator of saliva flow rate and certain clinical conditions; and
(iii) the gingival sulcus where the pH is an indication of periodontal disease severity.

Secondly, in medicine, for measuring the pH (acidity and alkalinity) in the esophagus or the stomach on a continuous 24-hour basis.

Thirdly, in medicine for measuring and monitoring the pH subcutaneously in connective tissue or muscle, as an early warning sign of an inadequate supply of oxygen in surgery, shock, critical care monitoring, anesthesia, fetal anoxia, and a number of other clinical applications, as opposed for example, to measuring or monitoring blood pH (which is a late sign). It can also be used for continuous intra-arterial and intra-venous pH monitoring. Tissue pH can be related to perfusion of the tissue and to its aerobic/anaerobic metabolism.

The general purpose microsize pH combination electrode can be used to monitor or measure pH in human or animal tissue or muscles, or organs, in blood, in fluid of calibrated buffers or other media such as beef, poultry, potatoes, apples, fruits and other food products. The electrode delivers a pH signal (or millivolt signal) to an appropriate pH meter designed especially for the metal oxide sensor in combination with the calomel half cell.

This electrode and its system of measurement are unique for the following reasons:
(a) It is microsize and can be made to fit into a #16 gauge steel needle or into a #16 gauge placement catheter and measures the pH at a localized position in the organ due to the immediated adjacency of the sensor electrodes; (b) Because it is microsize, the response time is very short and is much faster measuring hydrogen ion concentration than the traditional glass instruments; (c) It is robust and rugged and its design lends itself to ease of manufacture so it can be made disposable and will contain costs without compromising quality of health care; (d) It will enhance the quality of medical care, by acting as the earliest warning sign of a deteriorating physiological situation; (e) Because of its low cost it can be made disposable thus avoiding cross contamination; (f) It can easily be sterilized either ETO, or linear accelerator sterilized, which is also true for the ion bridge and buffer pads.

(g) Because of its design the electrode can be stored for long periods of time since it only becomes active when the reservoir is charged with gel, when the electrode is ready to be used.

(h) The proximity of the sensing electrode to the salt bridge through the use of a double lumen tube ensures quick, accurate response and most importantly very little if any drift. The proximity of sensor and bridge is the major benefit of this invention. In the media being measured the sensor electrode and the bridge are very close (approx. 0.020 inches apart).

(i) The microsize pH combination electrode is especially useful for physiological monitoring on a continuous basis in human or animal, tissue, muscle, organs or blood. It can be used to monitor or measure muscle or tissue pH in 1. neonates
  2. high risk or surgical patients (cardiovascular, open heat, by pass, others)
  3. patients in shock when all vital signs are shut down
  4. surgical intensive care, coronary care units, intensive care units.
  5. fetal scalp pH to detect anoxia
  6. in conjunction with cardiac out, for which it is the yardstick measurement
  7. brain tissue pH, neurology (j) The general purpose, microsize, combination pH hydrogen ion concentration sensor may be incorporated into a fetal scalp electrode to monitor both heart rate and fetal scalp pH as a reflection of fetal anoxia.

(k) The electrode enables early measurement of tissue or muscle perfusion. There is presently no way to assess this. The best that can be done now is to measure the pH of the blood either in vivo or in vitro, at great expense and risk; but most importantly, the present methods are very late signs because blood is well buffered and only shows a pH shift long after the problem has set in. Where blood pH determination may show a decrease in one hour after the problem has set in, muscle or tissue pH using the present invention will show a significant drop in pH in 2–3 minutes after the tissue or muscle is compromised for lack of perfusion with blood and life supporting oxygen.

(l) The methodology of the invention is minimally invasive, inexpensive, disposable, cost containing, and requires relatively simple instrumentation compared to present day methodologies, either with drawn blood samples or in vivo continuous monitoring. The currently used techniques are costly, traumatic, invasive and slow.

(m) It can be used in smaller, regional hospitals since it does not require the skills and expertise of laboratories or expert medical specialists.

(n) The use of an ion conducting gel that is thixotropic and free of fungus growth prevents leaching of KCl into the media being monitored, increases shelf life and enhances storage capability of salt bridges and electrodes.

Figure 2:
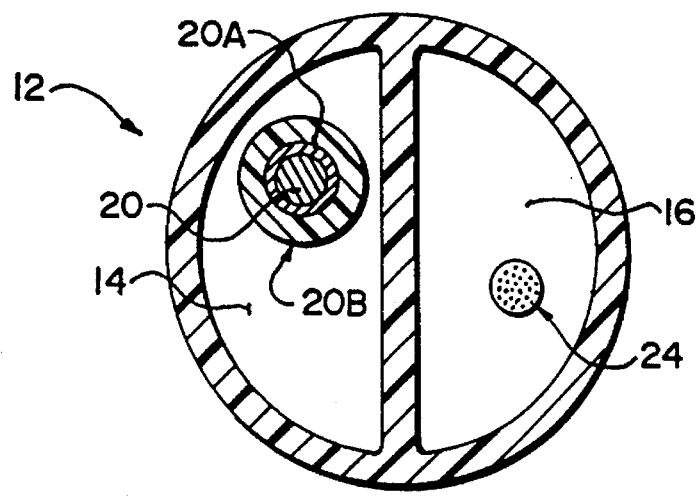
FIG. 2 is a transverse cross section of the electrode tube.

(o) The very microsize antimony sensor FIG. 2 is unique in its construction and design. Because of its very microsize the combination electrode is very responsive. The antimony is robust, never deteriorates with age; it can be wiped and cleaned of protein or other deposits. Because it is so microsize it does not cause tissue or muscle or organ necrosis.

(p) Because the electrode is used in a minimally invasive method it can easily be removed for recalibration and examination without patient discomfort or trauma.

(q) The antimony oxide electrode is a relatively low impedance device compared with the standard glass. Whereas the impedance of glass is 12 M$\Omega$, the impedance of the antimony is only 1 M$\Omega$. Consequently, no shielding is required.

Figure 6:
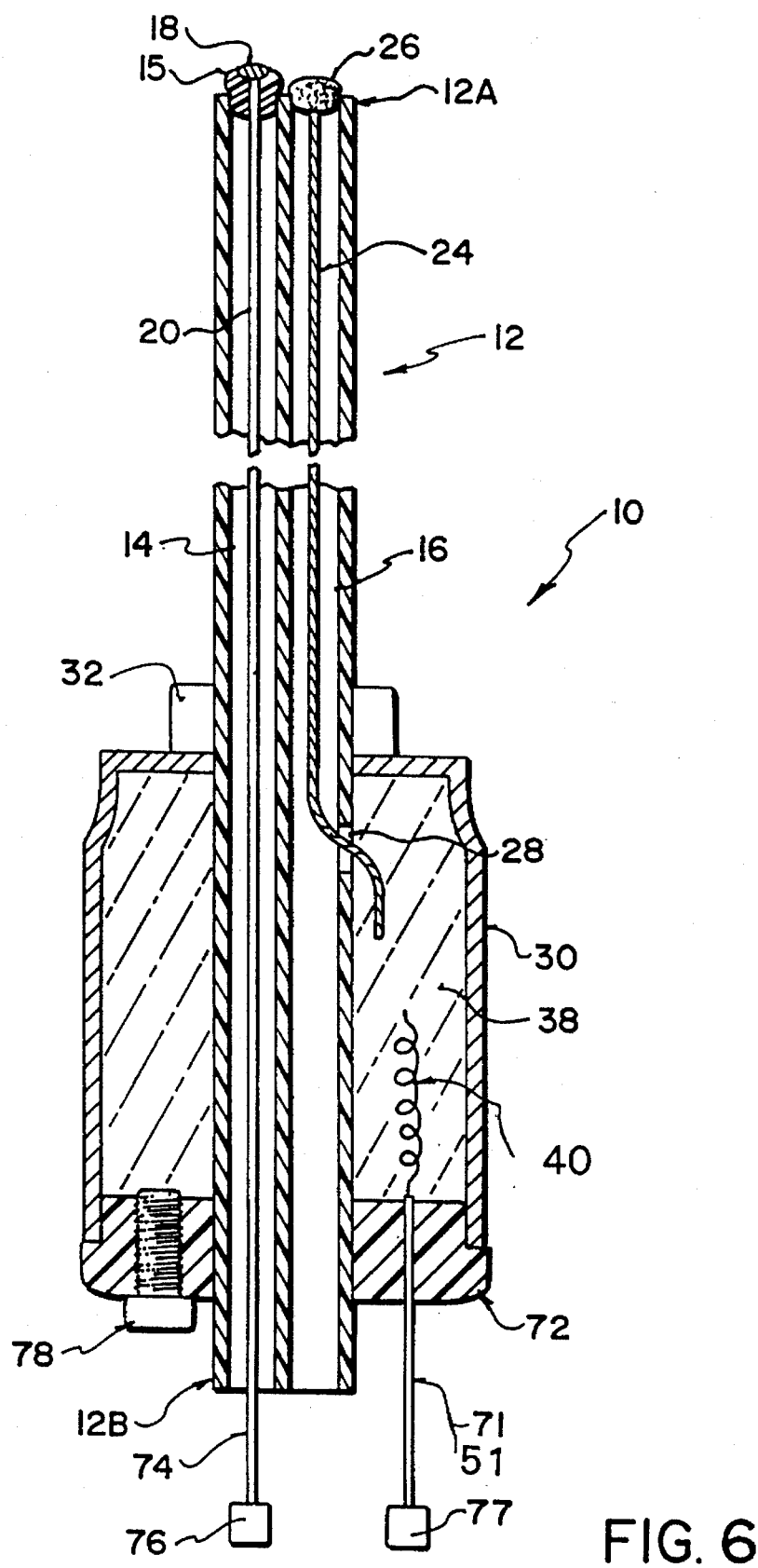
FIG. 6 is a schematic of a system in accordance with a second embodiment of the invention.

In FIG. 6 is shown an alternative arrangement to the Calomel reference of FIG. 1 which uses a silver/silver chloride reference mounted directly in the pH electrode element itself.

The alternate reference is a thin, 4 inch, silver/silver chloride wire 40 coiled to fit into the chamber or reservoir 30 of the combination electrode, One end of the silver/silver chloride wire 70 terminates in the chamber 30, the other end, first epoxied and then insulated with a plastic sleeve 70 that comes up through the cap 72 on the chamber, parallel to the antimony lead. The antimony lead shown at 74 and the silver/silver chloride lead 70, form the two bipolar leads at terminals 76 and 77 that measure the potential between them.

The reference 50 is connected through the gel junction 38 to the

The complete pH measuring system consists of the pH microsize electrode and several other components, for example a reference electrode, disposable buffers for calibration, a buffer pad holder, a pH meter and printer, and connectors for coupling the components. The pH electrodes, references, and calibrating buffers may be sterilizable and disposable. In some applications the pH electrode can be reusable.

The arrangement of FIG. 6 is also modified in that the end cap 72 includes the filler plug 78 so that the side of the chamber is not perforated as in FIG. 1.

Since various modifications can be made in my invention as hereinabove described, and many apparently widely different embodiments of same made within the spirit and scope of the claims without departing from such spirit and scope, it is intended that all matter contained in the accompanying specification shall be interpreted as illustrative only and not in a limiting sense.

We claim:

1. A pH measuring electrode comprising:

probe means for defining a first lumen and a second lumen with adjacent first ends;

a sensor electrode secured to the first end of the first lumen and exposed at the first end of the first lumen;

an electric conductor leading from the sensor electrode through the first lumen including means for electrical connection to an electrical meter for measuring an electrical value indicative of the pH to be measured;

a fibrous thread material extending along the second lumen;

means for electrically connecting the thread material to the electrical meter; and porous means closing the first end of the second lumen and electrically connected to the thread material.

2. An electrode according to claim 1 including a chamber connected to the second lumen for receiving an electrolytic gel, the thread extending from the second lumen into the chamber.

3. An electrode according to claim 2 including a filling port to the chamber and removable means for closing the filling port.

4. An electrode according to claim 2 including means for filling the chamber with the electrolytic gel.

5. An electrode according to claim 2 wherein the thread material carries an electrolyte which is in electrical connection with the electrolytic gel in the chamber.

6. An electrode according to claim 2 wherein the probe comprises a tube defined by said first and second lumens, the tube passing through the chamber and having a window formed in the second lumen for communication of the second lumen with the chamber and with the first lumen being sealed from the chamber.

7. An electrode according to claim 1 wherein the thread material carries an electrolyte.

8. An electrode according to claim 7 including electrical reference means in electrical connection with the electrolyte.

9. An electrode according to claim 8 wherein the electrical reference means is located in the chamber.

10. An electrode according to claim 1 wherein the probe comprises a tube defined by said first and second lumens.

11. An electrode according to claim 1 wherein the second lumen comprises a non-porous, non-metallic, flexible tubular duct, and a liquid contained in the duct for transmitting electrical signals by ion transfer.

12. An electrode according to claim 1 wherein the porous means is fibrous.

13. An electrode according to claim 1 wherein the thread is fibrous.

14. An electrode according to claim 1 including an ion bridge for connecting said thread to said electrical meter comprising a non-porous, non-metallic, flexible tubular duct, a liquid contained in the duct for transmitting electrical signals by ion transfer and a non-metallic conductive plug at an end of the duct for electrically connecting to the organ or patient.

15. A pH measuring electrode comprising:
   probe means for defining a first lumen and a second lumen with adjacent first ends;
   a sensor electrode secured to the first end of the first lumen and exposed at the first end of the first lumen;
   an electrical conductor leading from the sensor electrode through the first lumen including means for electrical connection to an electrical meter for measuring an electrical value indicative of the pH to be measured;
   a chamber connected to the second lumen, the chamber being arranged to receive an electrolytic liquid;
   electrical reference means in electrical connection with the electrolytic liquid
   means for electrically connecting the reference means to the electrical meter; and
   porous means closing the first end of the second lumen and electrically connected to the electrolytic liquid.

16. An electrode according to claim 16 wherein the porous means includes interstices impregnated with the liquid for allowing the liquid to provide conductivity through the porous means, the porous means preventing bleeding or leeching of the liquid.

17. An electrode according to claim 15 wherein the probe comprises a tube defined by said first and second lumens, the tube passing through the chamber and having a window formed in the second lumen for communication of the second lumen with the chamber and with the first lumen being sealed from the chamber.

18. An electrode according to claim 15 wherein the electrical reference means is located in the chamber.

\* \* \* \* \*